United States Patent [19]

VandenBerg

[11] Patent Number: Plant 7,531

[45] Date of Patent: May 21, 1991

[54] CHRYSANTHEMUM PLANT NAMED SANDY

[75] Inventor: Cornelis P. VandenBerg, Salinas, Calif.

[73] Assignee: Yoder Brothers, Inc., Barbeton, Ohio

[21] Appl. No.: 459,364

[22] Filed: Dec. 29, 1989

[51] Int. Cl.[5] ..... A01H 5/00

[52] U.S. Cl. ..... Plt./74

[58] Field of Search ..... Plt./74

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Sandy particularly characterized by its flat capitulum form; daisy capitulum type; soft honey-bronze ray floret color; diameter across face of capitulum of from 63 to 73 mm when fully opened; spreading and profile branching pattern; average natural season flower date of August 28 in Salinas, Calif. and September 27 in Hightstown, N.J.; uniform seven week photoperiodic flowering response to short days in photoperiodic controlled flowering programs; and durable, uniform performance.

3 Drawing Sheets

The present invention comprises a new and distinct cultivar of Chrysanthemum, botanically known as *Dendranthema grandiflora,* and referred to by the cultivar name Sandy.

Sandy, identified as 86-48801, was originated by the inventor Cornelis P. VandenBerg from a cross made in a controlled breeding program in Salinas, Calif., in 1986.

The female parent of Sandy was the cultivar identified as Triumph, a bronze decorative disclosed in U.S. Plant Pat. No. 5,995. The male parent of Sandy was the cultivar identified as Allure, a yellow daisy disclosed in U.S. Plant Pat. No. 5,989.

Sandy was discovered and selected as one flowering plant within the progeny of the stated cross by Cornelis P. VandenBerg in September 1986, in a controlled environment in Salinas, Calif.

The first act of asexual reproduction of Sandy was accomplished when vegetative cuttings were taken from the initial selection in November 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Sandy are firmly fixed and are retained through successive generations of asexual reproduction.

Sandy has not been observed under all possible environmental conditions. The phenotype may vary significantly with variations in environment such as temperature, light intensity and daylength.

The following observations, measurements and comparisons describe plants grown in controlled open areas in Salinas, Calif. and in Hightstown, N.J., and photoperiodic controlled programs conducted in Salinas, Calif. Rooted cuttings were established in soil and maintained outdoors under the natural temperature and daylength prevailing during June through October. Single pinching was practiced with all branches and buds retained.

The following traits have been repeatedly observed and are determined to be basic characteristics of Sandy, which, in combination, distinguish this Chrysanthemum as a new and distinct cultivar:

1. Flat capitulum form.
2. Daisy capitulum type.
3. Soft honey-bronze ray floret color.
4. Diameter across face of capitulum of 63–67 mm when fully opened.
5. Spreading and prolific branching pattern, with 7–8 branches after pinch two weeks after planting a rooted cutting in Hightstown, N.J.
6. Average natural season flower date of August 28 in Salinas, Calif., and September 27 in Hightstown, N.J., based on several years of trial flowering.
7. Uniform seven week photoperiodic flowering response to short days in photoperiodic controlled flowering programs.
8. Durable, uniform performance.

The accompanying photographic drawings show typical inflorescence and leaf characteristics of Sandy, with the colors being as nearly true as possible with illustrations of this type.

Sheet 1 is a color photograph of Sandy grown as pinched spray pot mum in a 15 cm pot.

Sheet 2 is a black and white photograph of three views of the inflorescence of Sandy.

Sheet 3 is a black and white photograph showing the upper and under sides of the leaves of Sandy at three stages of development (mature, intermediate and immature).

Of the commercial garden mum cultivars known to the inventor, the most similar in comparison to Sandy is the cultivar identified as Wolverine, an orange-bronze spoon tipped daisy disclosed in U.S. Plant Pat. No. 4,312. Reference is made to attached Chart A, which compares certain characteristics of Sandy to the same characteristics of Wolverine.

Similar traits are diameter across face of capitulum, controlled response, and what could be described generally as a bronze flower color. However, Sandy is a soft honey-bronze, with a daisy capitulum type, while Wolverine is an orange-bronze, with a spoon-tipped daisy capitulum type. Sandy is therefore a very distinctive new cultivar. Sandy has a more spreading and prolific branching pattern, and an earlier natural season flower date in New Jersey than Wolverine.

In the following description color references are made to The Royal Horticultural Society Colour Chart. The exact floret color of Sandy is not represented in The R.H.S. Colour Chart, and the color values given are those closest to the actual color of Sandy. The color values were determined on plant material grown in a controlled greenhouse environment in Salinas, Calif. on Sep. 19, 1989.

Classification:

*Botanical.*—*Dendranthema grandiflora* cv Sandy.

*Commercial.*—Flat daisy spray pot mum and garden mum.

INFLORESCENCE

A. Capitulum:

*Form.*—Flat.

*Type.*—Daisy.

*Diameter across face.*—63 to 73 mm when fully opened.

B. Corolla of ray florets:

*Color (general tonality from a distance of three meters).*—Soft honey-bronze.

*Color (upper surface).*—Closest to 13C, very slightly tinged with 24B.

*Color (under surface).*—Closest to 12B to 12C.

*Shape.*—Flat, straight, oblong.

C. Corolla of disc florets:

*Color (mature).*—14A to 14B.

*Color (immature).*—Closest to 14B, slightly tinged with 151A.

D. Reproductive organs:

*Androecium.*—Present on disc florets only; moderate pollen.

*Gynoecium.*—Present on both ray and disc florets.

PLANT

A. General appearance:

*Height.*—Average 29–30 cm. at time of flowering, based on June 14 planting in Hightstown, N.J.

*Branching pattern.*—Spreading and prolific.

B. Foliage:

*Color (upper surface).*—147A.

*Color (under surface).*—147B.

*Shape.*—See photograph.

CHART A

COMPARISON OF SANDY AND WOLVERINE

| CHARACTERISTIC | SANDY | WOLVERINE |
|---|---|---|
| Ray floret color | Honey-bronze | Orange-bronze |
| Capitulum Form and Type | Flat daisy | Flat spoon-tipped daisy |
| Branching pattern | Spreading and prolific | Semi-spreading |
| Diameter Across Face of Capitulum | 63 to 73 mm | 63 to 73 mm |
| Controlled Response | 7 weeks | 7 weeks |
| Average Natural Season Flower date: | | |
| In Salinas, California: | August 28 | Not available |
| In Hightstown, New Jersey: | September 28 | October 2 |

Comparisons Made of Plants Grown Under Natural Season Outdoor Conditions In Salinas, California and in Hightstown, New Jersey

I claim:

1. A new and distinct Chrysanthemum plant named Sandy, as described and illustrated.

* * * * *

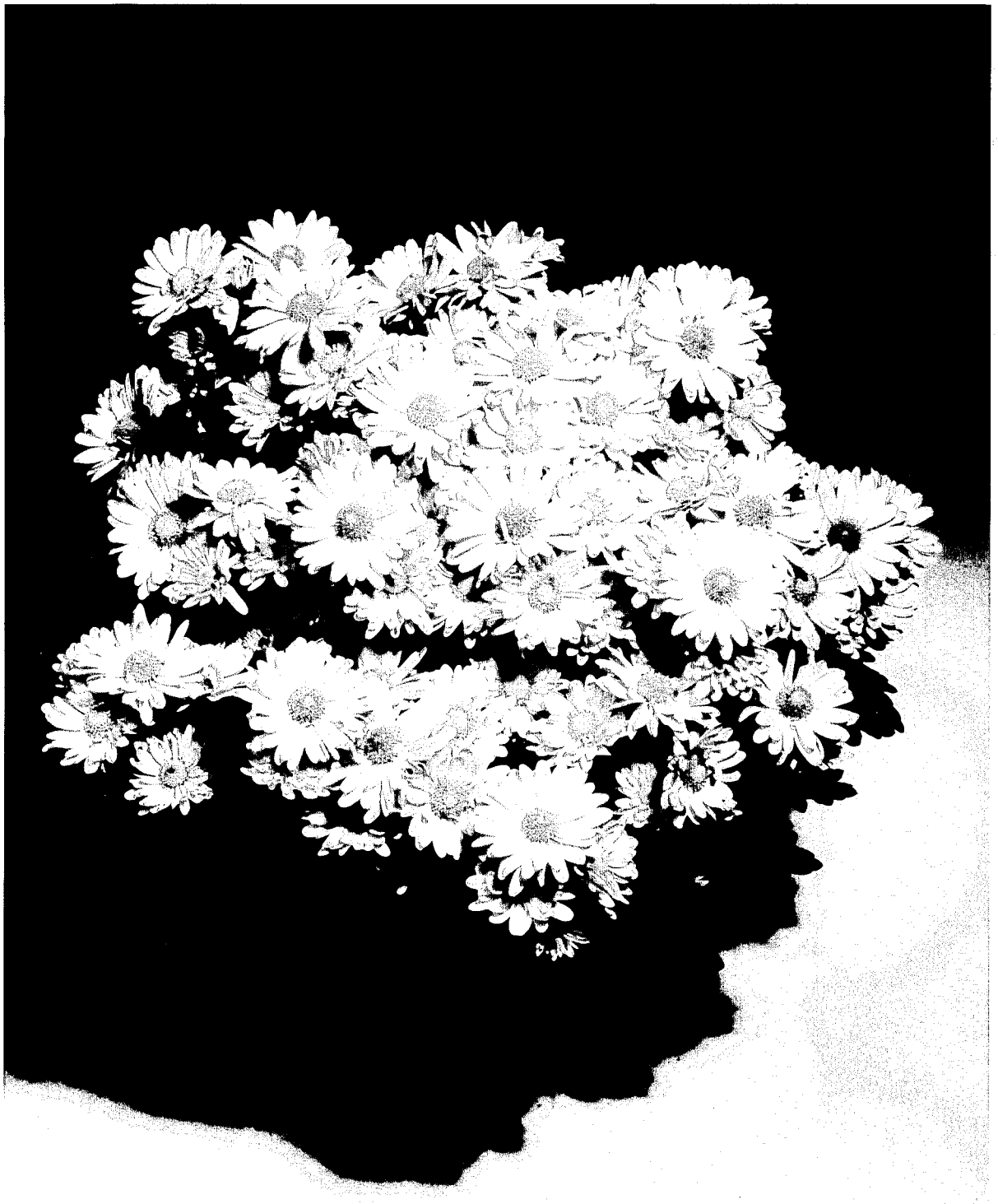

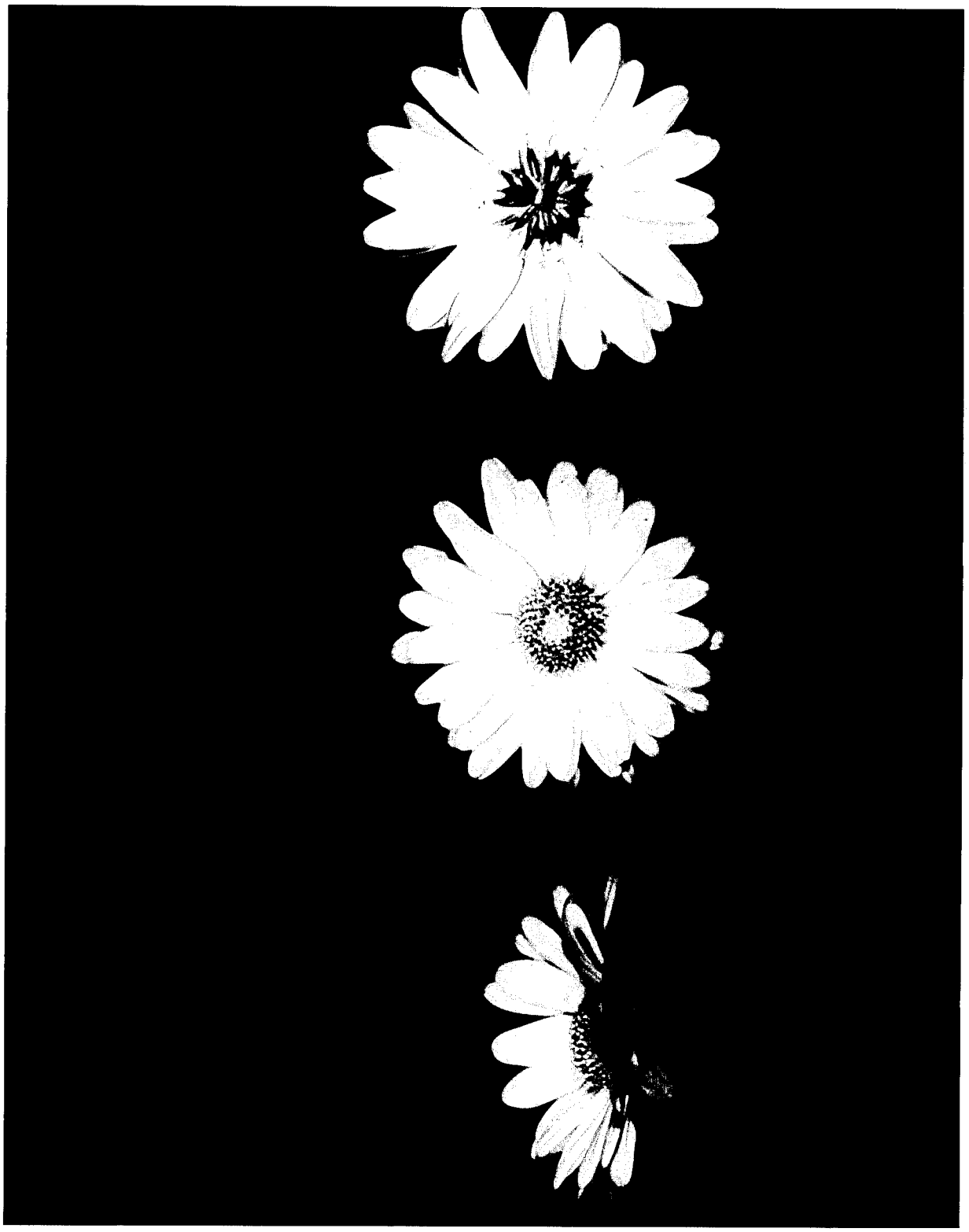

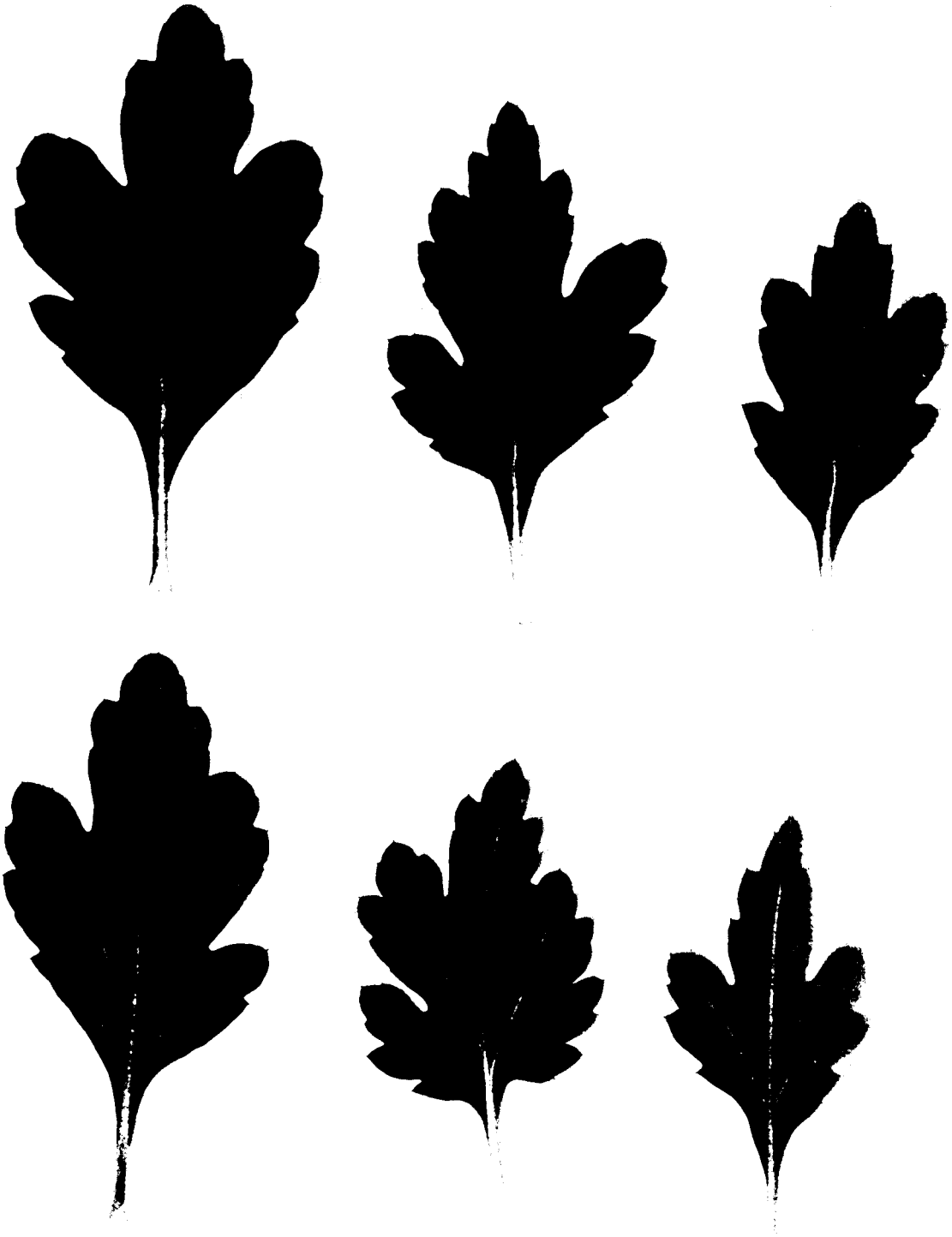

UNITED STATES PATENT AND TRADEMARK OFFICE

CERTIFICATE OF CORRECTION

PATENT NO. : PP7,531

DATED : May 21, 1991

INVENTOR(S) : Cornelis P. VandenBerg

It is certified that error appears in the above-identified patent and that said Letters Patent is hereby corrected as shown below:

Column 1, line 5, "86-48801" should be changed to --86-488001--

Column 2, line 8, "63-67 mm" should be changed to --63-73 mm--

In the Abstract (57), line 5, "profile" should be changed to --prolific--

Signed and Sealed this

Twenty-ninth Day of December, 1992

*Attest:*

*Attesting Officer*

DOUGLAS B. COMER

*Acting Commissioner of Patents and Trademarks*